(12) United States Patent
Spottiswoode et al.

(10) Patent No.: US 11,823,399 B2
(45) Date of Patent: Nov. 21, 2023

(54) MULTI-SCAN IMAGE PROCESSING

(71) Applicant: Siemens Medical Solutions USA, Inc., Malvern, PA (US)

(72) Inventors: Bruce Spottiswoode, Knoxville, TN (US); Vijay Shah, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 293 days.

(21) Appl. No.: 17/304,199

(22) Filed: Jun. 16, 2021

(65) Prior Publication Data

US 2022/0405948 A1    Dec. 22, 2022

(51) Int. Cl.
*G06T 7/00* (2017.01)
*G06T 7/30* (2017.01)
(Continued)

(52) U.S. Cl.
CPC .............. *G06T 7/30* (2017.01); *A61B 6/037* (2013.01); *A61B 6/5235* (2013.01); *A61B 6/5247* (2013.01); *G06T 3/0093* (2013.01); *G06T 5/001* (2013.01); *G06T 2207/10081* (2013.01); *G06T 2207/10088* (2013.01); *G06T 2207/10104* (2013.01); *G06T 2207/10108* (2013.01); *G06T 2207/20081* (2013.01); *G06T 2207/20084* (2013.01)

(58) Field of Classification Search
CPC ......... G06T 7/30; G06T 3/0093; G06T 5/001; G06T 2207/10081; G06T 2207/10088; G06T 2207/10104; G06T 2207/10108; G06T 2207/20081; G06T 2207/20084; G06T 7/0012; G06T 7/0014; G06T 5/50; G06T 7/337; G06T 2207/20104; G06T 2207/20221; G06T 2207/30016; G06T 2207/30048; G06T 2207/30061; G06T 2207/30096; A61B 6/037; A61B 6/5235; A61B 6/5247; A61B 6/032
See application file for complete search history.

(56) References Cited

U.S. PATENT DOCUMENTS

2011/0235884 A1\* 9/2011 Schreibmann ......... A61B 6/037
382/131
2018/0304099 A1\* 10/2018 Li ....................... A61B 5/0036
(Continued)

OTHER PUBLICATIONS

Armanious, K., Hepp, T., Küstner, T. et al. Independent attenuation correction of whole body FDG-PET using a deep learning approach with Generative Adversarial Networks. EJNMMI Res 10, 53 (2020).

(Continued)

*Primary Examiner* — Van D Huynh

(57) ABSTRACT

A framework for multi-scan image processing. A single real anatomic image of a region of interest is first acquired. One or more emission images of the region of interest are also acquired. One or more synthetic anatomic images may be generated based on the one or more emission images. One or more deformable registrations of the real anatomic image to the one or more synthetic anatomic images are performed to generate one or more registered anatomic images. Attenuation correction may then be performed on the one or more emission images using the one or more registered anatomic images to generate one or more attenuation corrected emission images.

20 Claims, 5 Drawing Sheets

(51) Int. Cl.
  *G06T 3/00*  (2006.01)
  *G06T 5/00*  (2006.01)
  *A61B 6/03*  (2006.01)
  *A61B 6/00*  (2006.01)

(56) References Cited

U.S. PATENT DOCUMENTS

2019/0311228 A1* 10/2019 Zhao ................ G06T 7/0014
2020/0258227 A1*  8/2020 Liao ................. G06T 7/0012
2021/0056734 A1*  2/2021 Han .................. A61B 5/7267
2022/0222873 A1*  7/2022 Shreshtha ............ G06T 7/64

OTHER PUBLICATIONS

Dong, Xue et al. "Synthetic CT generation from non-attenuation corrected PET images for whole-body PET imaging." Physics in medicine and biology vol. 64,21 215016. Nov. 4, 2019, doi:10.1088/1361-6560/ab4eb7.

Dong, Xue et al. "Deep learning-based attenuation correction in the absence of structural information for whole-body positron emission tomography imaging." Physics in medicine and biology vol. 65,5 055011. Mar. 2, 2020, doi:10.1088/1361-6560/ab652c.

Huan Yang, Pengjiang Qian, Chao Fan, "An Indirect Multimodal Image Registration and Completion Method Guided by Image Synthesis", Computational and Mathematical Methods in Medicine, vol. 2020, Article ID 2684851, 10 pages, 2020. https://doi.org/10.1155/2020/2684851.

* cited by examiner

MULTI-SCAN IMAGE PROCESSING

TECHNICAL FIELD

The present disclosure generally relates to image data processing, and more particularly to a framework for multi-scan image processing.

BACKGROUND

The field of medical imaging has seen significant advances since the time X-Rays were first used to determine anatomical abnormalities. Medical imaging hardware has progressed in the form of newer machines such as Medical Resonance Imaging (MRI) scanners, Computed Axial Tomography (CAT) scanners, etc. Digital medical images are constructed using raw image data obtained from such scanners. Digital medical images are typically either a two-dimensional ("2-D") image made of pixel elements or a three-dimensional ("3-D") image made of volume elements ("voxels"). Because of large amounts of image data generated in any given scan, there has been and remains a need for developing image processing techniques that can automate some or all of the processes to determine the presence of anatomical abnormalities in scanned medical images.

Multimodality imaging plays an important role in accurately identifying diseased and normal tissues. Multimodality imaging provides combined benefits by fusing images acquired by different modalities. The complementarity between anatomic (e.g., computed tomography (CT), magnetic resonance (MR)) and molecular (e.g., positron-emission tomography (PET), single-photon emission computerized tomography (SPECT)) imaging modalities, for instance, has led to the widespread use of PET/CT and SPECT/CT imaging.

Serial PET/CT (or SPECT/CT) involves a sequence of multiple scans (or multi-scans) to assess the status of the region of interest over a period of time. Serial PET/CT may be performed in a number of circumstances, including dosimetry assessment and multi-tracer studies. However, repeated scans may expose the patient to increased radiation risks.

SUMMARY

Described herein is a framework for multi-scan image processing. A single real anatomic image of a region of interest is first acquired. One or more emission images of the region of interest are also acquired. One or more synthetic anatomic images may be generated based on the one or more emission images. One or more deformable registrations of the real anatomic image to the one or more synthetic anatomic images are performed to generate one or more registered anatomic images. Attenuation correction may then be performed on the one or more emission images using the one or more registered anatomic images to generate one or more attenuation corrected emission images.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
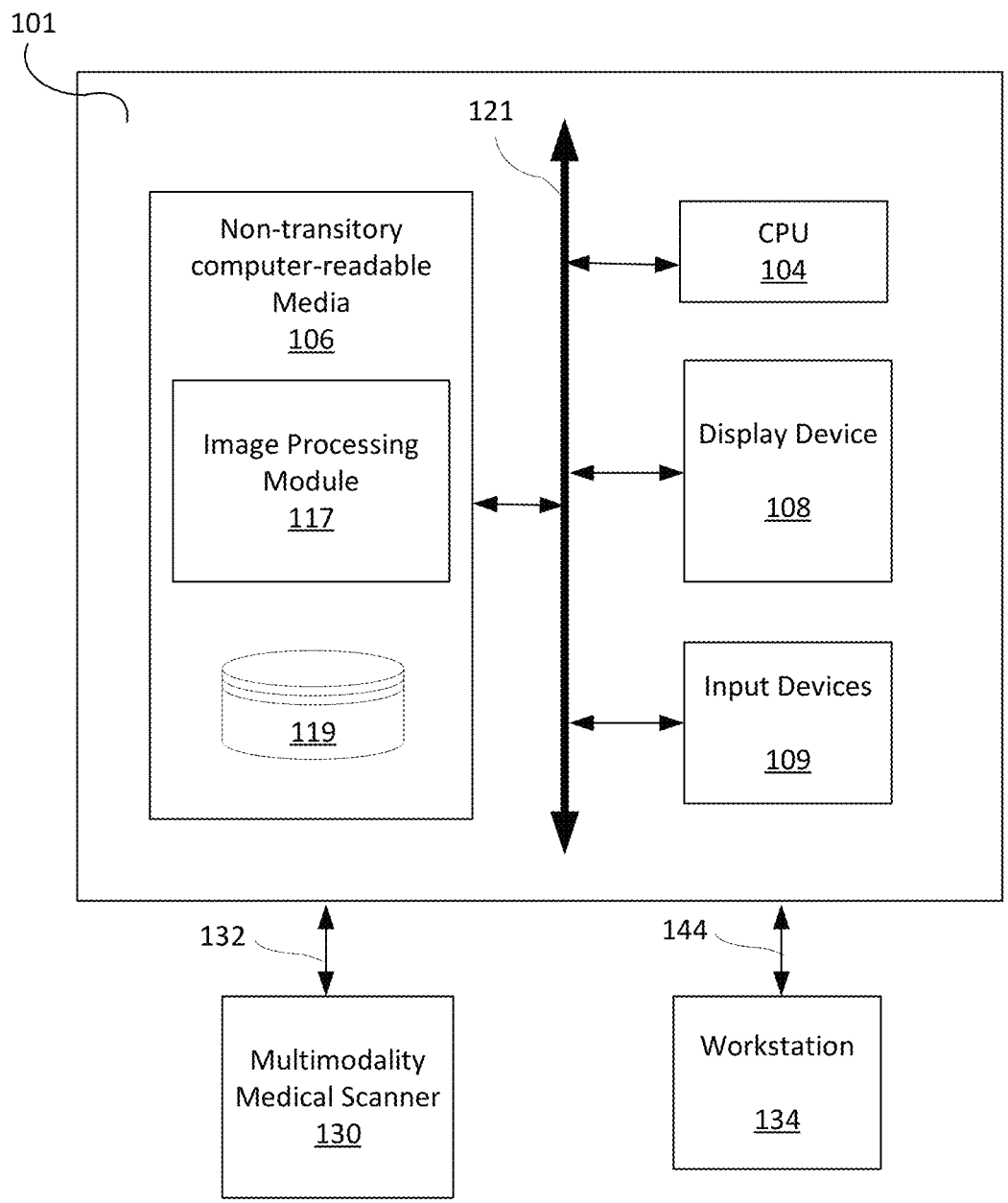
FIG. 1 shows a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

For brevity, an image, or a portion thereof (e.g., a region of interest (ROI) in the image) corresponding to an object (e.g., a tissue, an organ, a tumor, etc., of a subject (e.g., a patient, etc.)) may be referred to as an image, or a portion of thereof (e.g., an ROI) of or including the object, or the object itself. For instance, an ROI corresponding to the image of a lung or a heart may be described as that the ROI includes a lung or a heart. As another example, an image of or including a chest may be referred to a chest image, or simply a chest. For brevity, that a portion of an image corresponding to an object is processed (e.g., extracted, segmented, etc.) may be described as the object is processed. For instance, that a portion of an image corresponding to a lung is extracted from the rest of the image may be described as that the lung is extracted.

A CT scan is sometimes required only for attenuation correction and may offer little to no diagnostic advantage. Accumulated dose due to serial CT scans may be avoidable by registering the initial CT image to subsequent molecular imaging scans. However, registration between functional PET/SPECT images and structural CT images is not reliably possible using conventional methods, owing to the orthogonality (i.e. lack of mutual information) between image pairs.

Molecular and CT scans are typically acquired sequentially, so inter-scan patient motion leads to spatial mismatches between molecular and CT images. Spatial mismatch between molecular and CT scan images is largely not addressed in traditional systems. In some cases (e.g. cardiac), the CT image is rigidly translated to provide a better match, but this only offers regional corrections and a rigid translation is not a realistic representation. Current efforts are focused on directly estimating attenuation from the emission data. This may find utility in limited scenarios where the underlying anatomy is relatively consistent (e.g. cardiac or brain studies), but it is not suitable for whole body oncology scenarios where solid masses may appear in unusual places. Consider, for example, large solid tumors identifiable on the CT image but only some of these have significant radiotracer uptake. The CT image will not predict the attenuating masses without radiotracer uptake.

A framework for multimodality image registration is presented herein. In accordance with one aspect, an emission image (e.g., SPECT or PET) is registered to an anatomic image (e.g., CT) by generating a synthetic anatomic image from a non-attenuation corrected (NAC) emission image and using the synthetic anatomic image as a target for anatomic-to-anatomic image registration with the true anatomic image. Deforming a true anatomic image to the synthetic anatomic image may preserve all attenuating masses, and the true anatomic image may be made available for comparison in quality assurance. In areas without mutual information (e.g. unusual solid mass without radiotracer uptake), the deformation field is guided by surrounding structures and still be valid.

The present framework may be used for providing robust PET/CT, SPECT/CT, PET/MR registration, or other hybrid modality registration. Advantageously, it can be used to reduce dose accumulation and/or total scan time, thereby reducing the associated risks. Reducing radiation dose accumulation due to serial CT scans is particularly important in sensitive populations (e.g., pediatrics). These and other exemplary advantages and features will be described in more details in the following description.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as multimodality medical scanner 130 and workstation 134. In a networked deployment, computer system 101 may operate in the capacity of a server (e.g., in a server-client user network environment, a client user machine in server-client user network environment, or as a peer machine in a peer-to-peer (or distributed) network environment).

In one implementation, computer system 101 includes a processor device or central processing unit (CPU) 104 coupled to one or more non-transitory computer-readable media 106 (e.g., computer storage or memory device), display device 108 (e.g., monitor) and various input devices 109 (e.g., mouse, touchpad or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in one or more non-transitory computer-readable media 106. In particular, the present techniques may be implemented by an image processing module 117. Non-transitory computer-readable media 106 may include random access memory (RAM), read-only memory (ROM), magnetic floppy disk, flash memory, and other types of memories, or a combination thereof. The computer-readable program code is executed by CPU 104 to process data provided by, for example, database 119 and/or multimodality medical scanner 130. As such, the computer system 101 is a general-purpose computer system that becomes a specific-purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein. The same or different computer-readable media 106 may be used for storing a database 119, including, but not limited to, image datasets, a knowledge base, individual subject data, medical records, diagnostic reports (or documents) for subjects, or a combination thereof.

Multimodality medical scanner 130 acquires image data 132. Such image data 132 may be processed and stored in database 119. Multimodality medical scanner 130 may be a radiology scanner (e.g., nuclear medicine scanner) and/or appropriate peripherals (e.g., keyboard and display device) for acquiring, collecting and/or storing such image data 132. Multimodality medical scanner 130 may be a hybrid modality designed for acquiring image data using at least one anatomic imaging modality (e.g., CT, MR) and at least one molecular imaging modality (e.g., SPECT, PET). Anatomic imaging modality focuses on extracting structural information, while molecular imaging modality focuses on extracting functional information from molecules of interest. Multimodality medical scanner 130 may be, for instance, a PET/CT, SPECT/CT or PET/MR scanner.

The workstation 134 may include a computer and appropriate peripherals, such as a keyboard and display device, and can be operated in conjunction with the entire system 100. For example, the workstation 134 may communicate with multimodality medical scanner 130 so that the medical image data 132 from multimodality medical scanner 130 can be presented or displayed at the workstation 134. The workstation 134 may communicate directly with the computer system 101 to display processed data and/or output results 144. The workstation 134 may include a graphical user interface to receive user input via an input device (e.g., keyboard, mouse, touch screen, voice or video recognition interface, etc.) to manipulate visualization and/or processing of the data.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
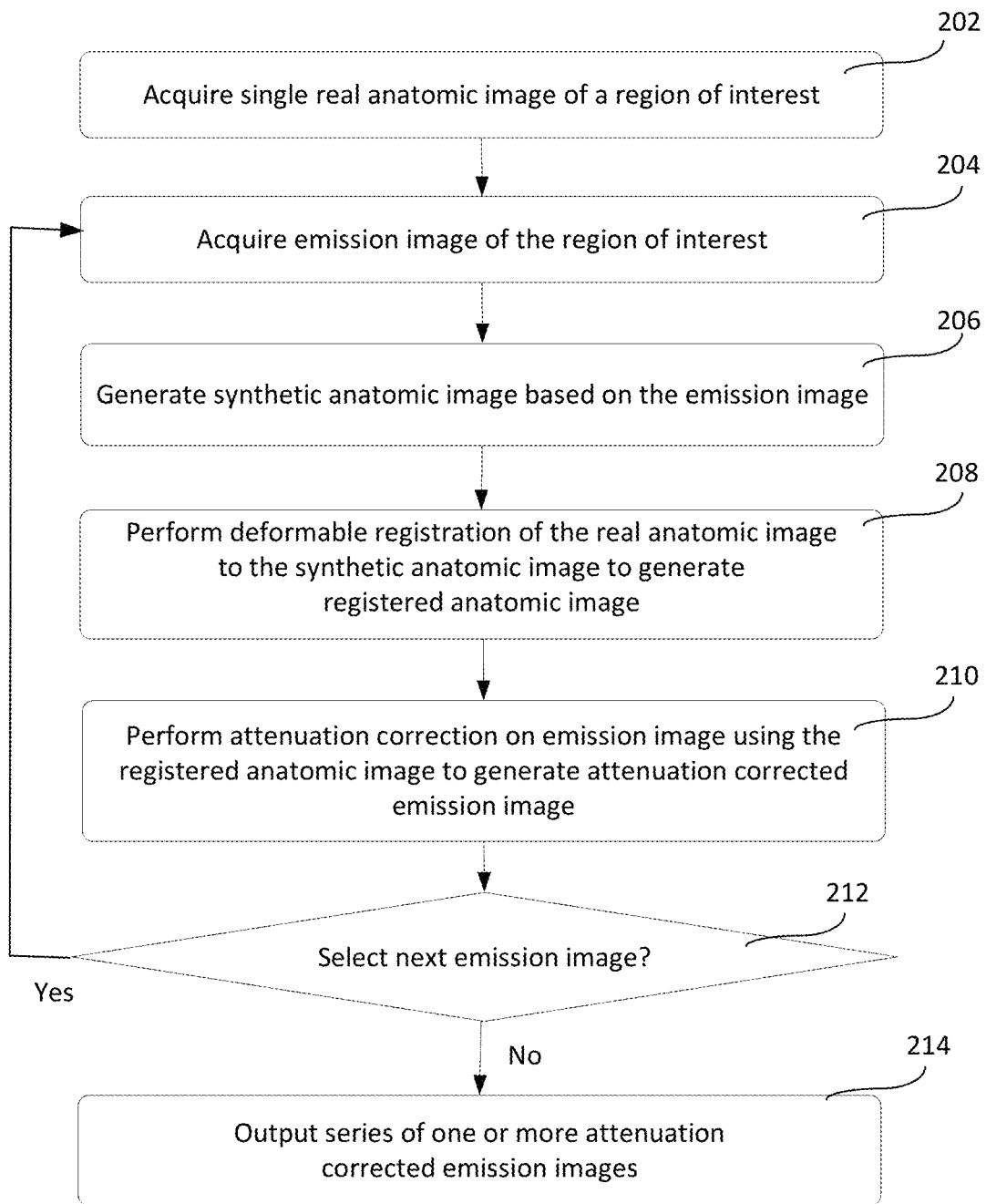
FIG. 2 shows an exemplary method of image processing.

FIG. 2 shows an exemplary method 200 of image processing. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, multimodality medical scanner 130 acquires a real anatomic image of a region of interest. More particularly, the anatomic imaging modality of the multimodality medical scanner 130 may directly acquire a single real anatomic image of a region of interest of a subject or patient. The real anatomic image may be, for example, a real CT or MR image. Other types of anatomic imaging modalities are also useful.

At 204, multimodality medical scanner 130 acquires an emission image of the region of interest. More particularly, the molecular imaging modality of the multimodality medical scanner 130 may directly acquire an emission image of the region of interest. The emission image is non-attenuation corrected (NAC). To generate the emission image, the molecular imaging modality may detect emissions generated by a radioactive isotope injected into the subject's bloodstream. In some implementations, the emission image is a PET or SPECT image. Other types of molecular imaging modalities are also useful.

At 206, image processing module 117 generates a synthetic (or pseudo) anatomic image of the region of interest based on the emission image. The synthetic anatomic image may be generated using artificial intelligence (or machine learning) techniques. For example, a deep learning algorithm based on generative adversarial networks (GANs), U-Nets or other image-to-image networks, may be implemented. The deep learning network may be trained to generate the synthetic anatomic image from the NAC emission image. Other types of artificial intelligence techniques are also useful.

Figure 3A:
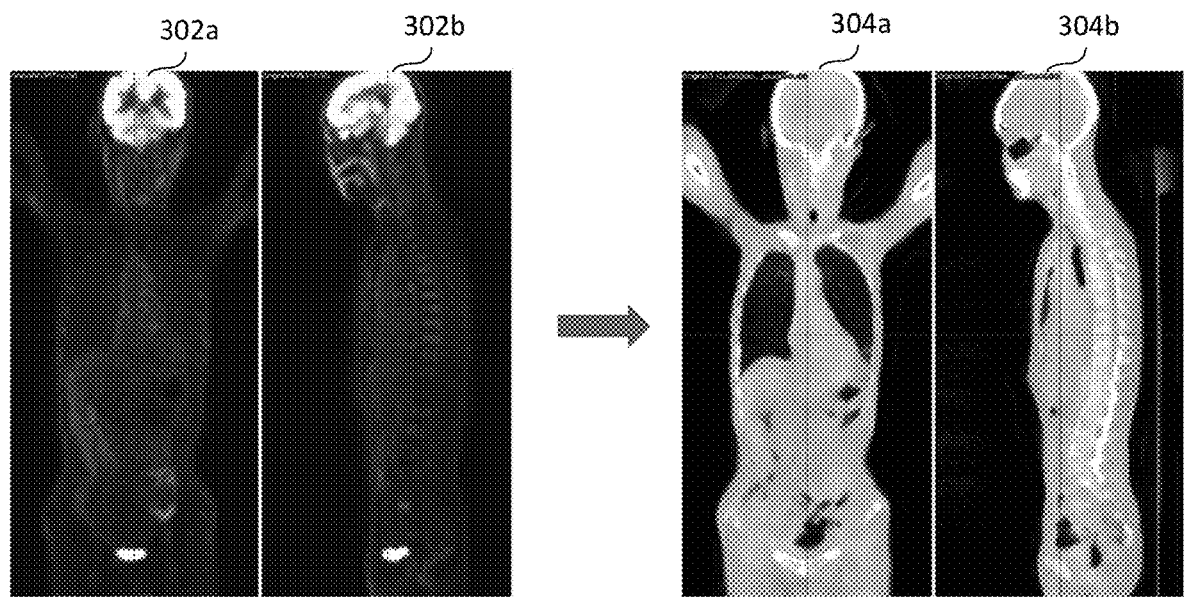
FIG. 3a shows exemplary anterior and posterior views of a non-attenuation corrected (NAC) PET image and a corresponding synthetic CT image.
Figure 3B:
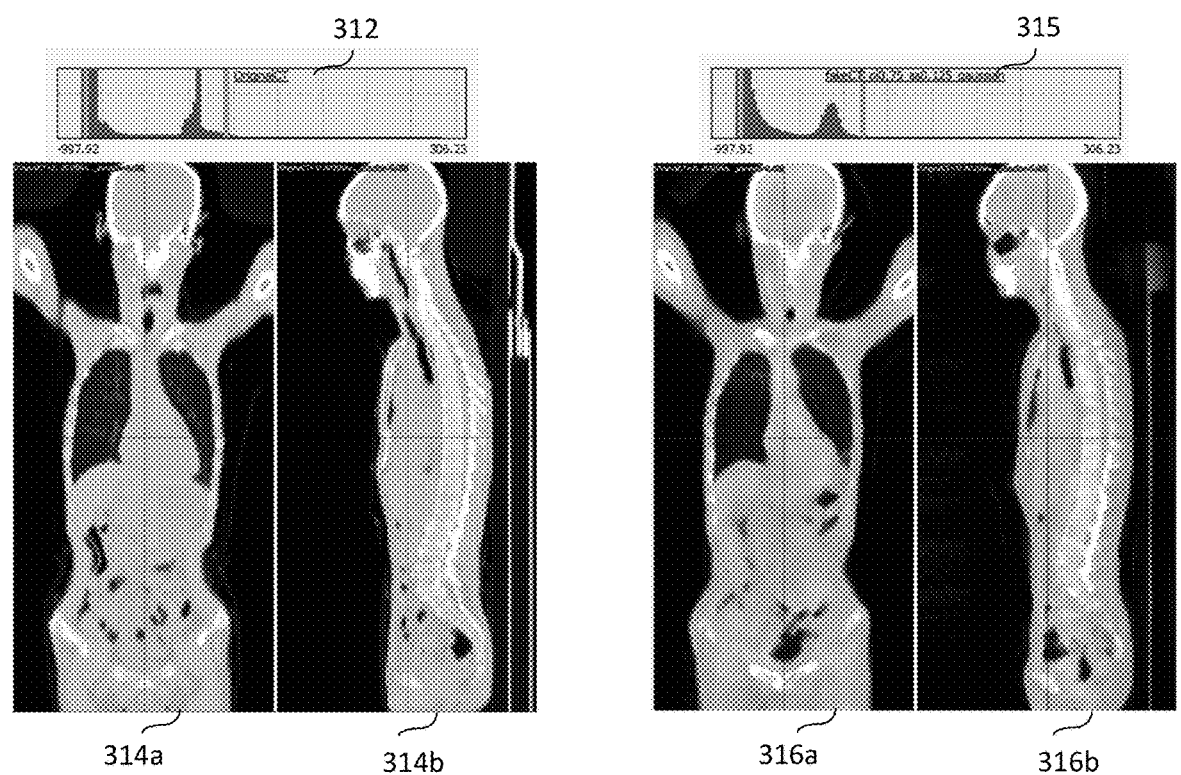
FIG. 3b shows an exemplary comparison of the real CT image with the synthetic CT image.

FIG. 3a shows exemplary anterior and posterior views 302a-b of the NAC PET image that is used to derive exemplary anterior and posterior views 304a-b of the synthetic CT image. FIG. 3b shows an exemplary comparison of the true (or real) CT image with the synthetic CT image. More particularly, the histogram 312 as well as the anterior and posterior views 314a-b of the true CT image is shown alongside the histogram 315 as well as the anterior and posterior views 316a-b of the synthetic CT image.

Returning to FIG. 2, at 208, image processing module 117 performs a deformable (or non-rigid) registration of the real anatomic image to the synthetic anatomic image to generate a registered anatomic image for improved attenuation correction. Deformable registration may be performed by finding a transformation that maps or aligns the source image to the target image by solving an objective function (e.g., similarity measure). In other implementations, deformable registration is performed by using a deep learning algorithm (e.g., neural networks) or other machine learning algorithms. In some implementations, the cross-modality registration process (i.e., steps 206 and 208) is implemented using a single neural network. Deformable registration is performed to register or spatially align the real anatomic image (source image) with the synthetic anatomic image (target image) to generate a registered real anatomic image.

Figure 4A:
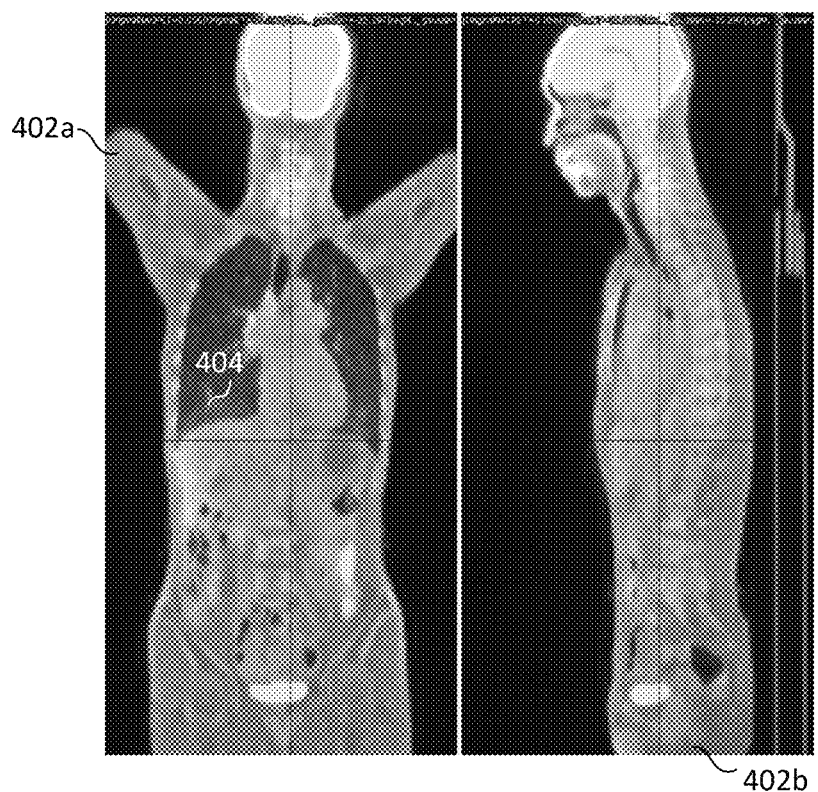
FIG. 4a shows anterior and posterior views of an exemplary resultant image obtained by overlaying a NAC PET image on the real CT image.
Figure 4B:
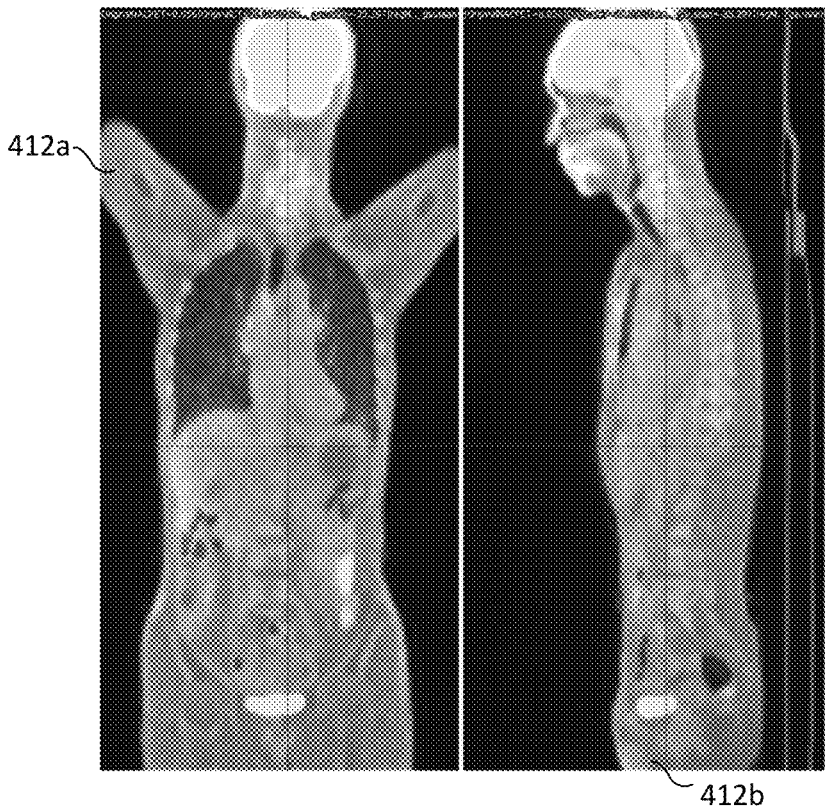
FIG. 4b shows anterior and posterior views of an exemplary resultant image obtained by overlaying a NAC PET image on the registered real CT image.

FIG. 4a shows anterior and posterior views 402a-b of an exemplary resultant image obtained by overlaying a NAC PET image on the real CT image. A spatial mismatch may be observed in the region 404. FIG. 4b shows anterior and posterior views 412a-b of an exemplary resultant image obtained by overlaying a NAC PET image on the registered real CT image. No spatial mismatch is observed in the resultant image.

Figure 5A:
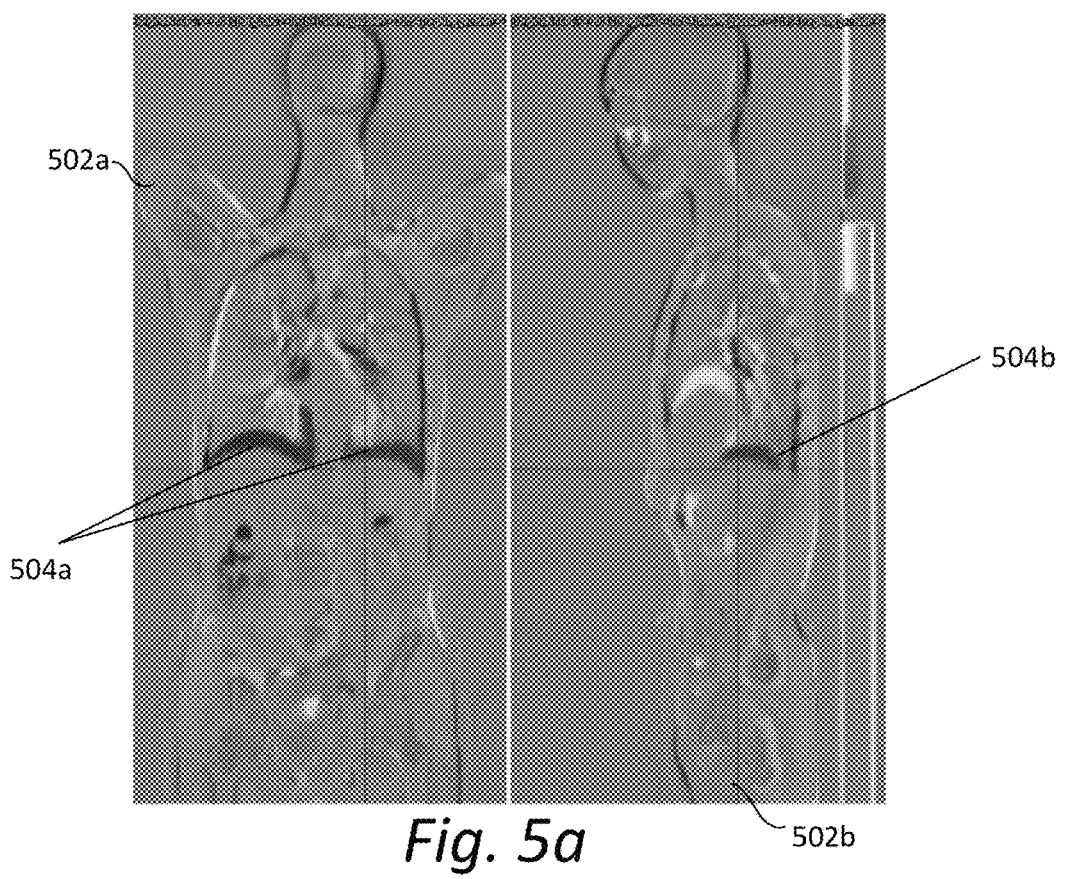
FIG. 5a shows anterior and posterior views an exemplary resultant image obtained by overlaying a real CT image on an inverted synthetic CT image.
Figure 5B:
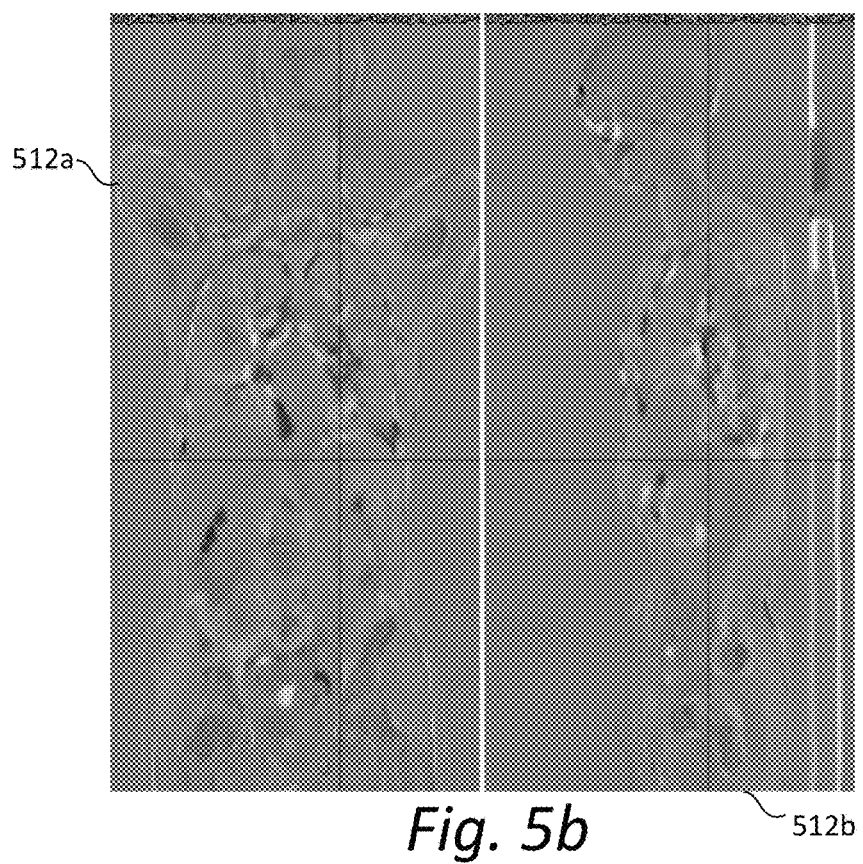
FIG. 5b shows anterior and posterior views of an exemplary resultant image obtained by overlaying a registered real CT image on an inverted synthetic CT image.

FIG. 5a shows anterior and posterior views 502a-b of an exemplary resultant quality control image obtained by overlaying a real CT image on an inverted synthetic CT image. A spatial mismatch may be observed in the regions 504a-b. FIG. 5b shows anterior and posterior views 512a-b of an exemplary resultant image obtained by overlaying a registered real CT image on an inverted synthetic CT image. No spatial mismatch is observed in the resultant image.

Returning to FIG. 2, at 210, image processing module 117 performs attenuation correction on the emission image using the registered anatomic image to generate attenuation corrected emission image. More particularly, from the attenuation coefficient data acquired with the registered anatomic image (e.g., CT image), correction factors may be determined and used to correct the emission image (e.g., SPECT, PET) for attenuation, yielding the attenuation-corrected emission image.

In some cases, it may be advantageous to move the emission image into the space of the real anatomic image. For example, if the real anatomic image is at a clinically more desirable spatial location or anatomical pose (e.g. deep inspiration breath hold CT is the radiological convention for lung imaging, but the emission image may be obtained in a different respiratory position), it is desirable to move the emission image into the anatomical space of the real anatomic image. Following the registration of the real anatomic image to the synthetic anatomic image and subsequent attenuation correction of the emission image, a post-processing step may optionally be performed. Such post-processing includes warping the attenuation-corrected emission image into the desired anatomical space of the real anatomic image using inverse deformation fields from the real-to-synthetic anatomic image registration in step 208. It should be appreciated that the attenuation correction of the emission image may also be performed after warping a non-attenuation corrected emission image into the desired anatomical space.

At 212, the selection of the next emission image is determined. If no next emission image is selected, the method 200 proceeds to 214. If the next emission image is selected, the method 200 returns to 204. Steps 204 through 212 may be repeated multiple times (e.g., 1, 2, . . . , N) over time to generate a set of attenuation corrected emission images using a single real anatomic image acquired in step 202. Advantageously, the acquisition of a single real anatomic image (instead of multiple anatomic images) reduces the scan time and/or radiation dose, thereby making the scan process more efficient and less risky due to accumulated dose from, for example, repeated CT image acquisition.

The multiple emission images may be acquired at different time points according to the present framework in various scenarios. For example, when multiple radiotracers are used in a single scan session, different emission images may be acquired after different radiotracers are injected in the subject. As another example, a series of multiple emission images may be acquired over time within a single scan session to perform temporal gating (e.g., for different respiratory or cardiac positions). A matched CT image may be created for each gate. Different spatial anatomical representations may be provided. As yet another example, multiple emission images may be acquired in a temporal series of scan sessions following the injection of a long-lived radioisotope in the subject's body for use in therapy. Examples of such therapy include alpha- or beta-emitter radionuclide therapy or Zr-based immunotherapy. As yet another example, multiple emission images may be acquired for monitoring therapy response, particularly in cases with rapid responses.

At 214, image processing module 117 outputs a series of one or more attenuation corrected emission images. Spatial mismatch between functional and anatomical images has been removed, enabling more accurate and precise attenuation correction. The one or more attenuation corrected emission images may be displayed at, for example, workstation 134.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. An image processing system, comprising:
   a non-transitory memory device for storing computer readable program code; and
   a processor device in communication with the memory device, the processor device being operative with the computer readable program code to perform steps including
   (i) acquiring a single real anatomic image of a region of interest,
   (ii) acquiring an emission image of the region of interest,
   (iii) generating a synthetic anatomic image based on the emission image,
   (iv) performing a deformable registration of the single real anatomic image to the synthetic anatomic image to generate a registered anatomic image, and
   (v) performing attenuation correction on the emission image using the registered anatomic image to generate an attenuation corrected emission image,
   wherein steps (ii), (iii), (iv) and (v) are repeated to generate a set of attenuation corrected emission images based on the single real anatomic image.

2. The system of claim 1 wherein the single real anatomic image comprises a real computed tomography (CT) or magnetic resonance (MR) image.

3. The system of claim 1 wherein the emission image comprises a positron-emission tomography (PET) or single-photon emission computerized tomography (SPECT) image.

4. The system of claim 1 wherein the processor device is operative with the computer readable program code to generate the synthetic anatomic image and perform the deformable registration of the single real anatomic image to the synthetic anatomic image using a single neural network.

5. The system of claim 1 wherein the processor device is operative with the computer readable program code to warp the attenuation corrected emission image into anatomical space of the single real anatomic image by using inverse deformation fields from the deformable registration of the single real anatomic image to the synthetic anatomic image.

6. The system of claim 1 wherein the processor device is operative with the computer readable program code to repeat step (ii) to acquire different emission images after different radiotracers are injected in a subject.

7. The system of claim 1 wherein the processor device is operative with the computer readable program code to repeat step (ii) to acquire a series of multiple emission images over time within a single scan session to perform temporal gating.

8. The system of claim 1 wherein the processor device is operative with the computer readable program code to repeat step (ii) to acquire multiple emission images in a temporal series of scan sessions following injection of a radioisotope in a subject for use in therapy.

9. An image processing method, comprising:
   (i) acquiring a single real anatomic image of a region of interest;
   (ii) acquiring one or more emission images of the region of interest;
   (iii) generating one or more synthetic anatomic images based on the one or more emission images;
   (iv) performing one or more deformable registrations of the single real anatomic image to the one or more synthetic anatomic images to generate one or more registered anatomic images; and
   (v) performing attenuation correction on the one or more emission images using the one or more registered anatomic images to generate one or more attenuation corrected emission images.

10. The method of claim 9 wherein acquiring the one or more emission images of the region of interest comprises acquiring different emission images after different radiotracers are injected in a subject.

11. The method of claim 9 wherein acquiring the one or more emission images of the region of interest comprises acquiring a series of multiple emission images over time within a single scan session to perform temporal gating.

12. The method of claim 9 wherein acquiring the one or more emission images of the region of interest comprises acquiring multiple emission images in a temporal series of scan sessions following injection of a radioisotope in a subject for use in therapy.

13. The method of claim 9 wherein acquiring the single real anatomic image comprises acquiring a real computed tomography (CT) or magnetic resonance (MR) image.

14. The method of claim 9 wherein acquiring the one or more emission images comprises acquiring a positron-emission tomography (PET) or single-photon emission computerized tomography (SPECT) image.

15. The method of claim 9 wherein generating the one or more synthetic anatomic images based on the one or more emission images comprises applying a deep learning algorithm.

16. The method of claim 9 further comprises warping the one or more attenuation corrected emission images into anatomical space of the single real anatomic image using inverse deformation fields from the one or more deformable registrations.

17. The method of claim 9 further comprises warping, prior to performing the attenuation correction, the one or more emission images into anatomical space of the single real anatomic image using inverse deformation fields from the one or more deformable registrations.

18. The method of claim 9 wherein generating the one or more synthetic anatomic images and performing the one or more deformable registrations are performed using a single neural network.

19. One or more non-transitory computer-readable media embodying instructions executable by a machine to perform operations for image processing comprising:
(i) acquiring a single real anatomic image of a region of interest;
(ii) acquiring an emission image of the region of interest;
(iii) generating a synthetic anatomic image based on the emission image;
(iv) performing a deformable registration of the single real anatomic image to the synthetic anatomic image to generate a registered anatomic image; and
(v) performing attenuation correction on the emission image using the registered anatomic image to generate an attenuation corrected emission image,
wherein steps (ii), (iii), (iv) and (v) are repeated to generate a set of attenuation corrected emission images based on the single real anatomic image.

20. The one or more non-transitory computer-readable media of claim 19 wherein the single real anatomic image comprises a real computed tomography (CT) or magnetic resonance (MR) image.

* * * * *